US005433211A

United States Patent [19]

Brammer et al.

[11] Patent Number: 5,433,211
[45] Date of Patent: Jul. 18, 1995

[54] METHOD AND SYSTEM FOR IDENTIFYING VIBROTACTILE PERCEPTION THRESHOLDS OF NERVE ENDINGS WITH INCONSISTENT SUBJECT RESPONSE REJECTION

[75] Inventors: Anthony J. Brammer; Joseph E. Piercy, both of Gloucester, Canada

[73] Assignee: National Research Council of Canada, Ottawa, Canada

[21] Appl. No.: 92,874

[22] Filed: Jul. 19, 1993

[51] Int. Cl.$^6$ .................. A61B 5/00; G06F 15/00
[52] U.S. Cl. .................. 128/739; 364/413.01
[58] Field of Search .................. 364/413.01, 413.02; 128/677, 678, 739, 743, 744, 774, 782

[56] References Cited

U.S. PATENT DOCUMENTS

| | | | |
|---|---|---|---|
| 5,002,065 | 3/1991 | LaCourse et al. | 128/739 |
| 5,022,407 | 6/1991 | Horch et al. | 128/739 |
| 5,195,532 | 3/1993 | Schumacher et al. | 128/739 |

*Primary Examiner*—Gail O. Hayes
*Assistant Examiner*—Khai Tran

[57] ABSTRACT

A method of identifying vibrotactile perception thresholds of tactile nerve endings at a skin site of a subject to assess sensory change in sensory nerve function is disclosed in which the results are substantially void of errors or inconsistencies. The measurement technique involves supporting the body part containing the skin site to be studied, and stimulating the skin surface with vibration under controlled contact conditions in such a way that the threshold at each frequency is mediated by a single mechanoreceptor population. Two known frequencies, within the range of frequencies in which the thresholds are mediated by the same mechanoreceptor population are applied to the skin site and this process is repeated for different mechanoreceptor populations. At each frequency of measurement, sensory responses are obtained from the subject as the vibration amplitude is increased and decreased. These responses are converted into threshold signals from which threshold shift values are established, by reference to normative values, the deviation of which is then compared with a reference inconsistency limit value derived from healthy persons, in order to determine the acceptance or rejection of the threshold signal values derived from the subject. If the threshold signal values are rejected, the test is repeated until acceptable threshold signal values are obtained thereby providing a true response of the subject.

19 Claims, 10 Drawing Sheets

METHOD AND SYSTEM FOR IDENTIFYING VIBROTACTILE PERCEPTION THRESHOLDS OF NERVE ENDINGS WITH INCONSISTENT SUBJECT RESPONSE REJECTION

TECHNICAL FIELD

The present invention relates to a method of identifying vibrotactile perception thresholds of nerve endings at a skin site of a subject to assess sensory change in tactile sensory nerve function, and wherein the resultant threshold signals obtained by the method are substantially void of errors or inconsistencies.

BACKGROUND ART

Recent research has shown the tactile performance of the hand to be critically dependent on neural activity in up to four populations of specialized nerve endings. These nerve endings respond differently to disturbances in the skin surface. This is disclosed in an article by Johansson R S, Vallbo A B. Tactile sensory coding in the glabrous skin of the human hand. Trends in Neuroscience 6 (1983) 27-32. Although the relationships between neural codes from individual mechanoreceptor populations and the detection of surface topography and texture have not been completely established, they are known to involve information from three mechanoreceptor types (SAI—slow adapting type I, FAI—fast adapting type I, and FAII—fast adapting type II). The roles of different receptor populations are discussed in the following two articles, namely, Johnson K O, Phillips J R. Spatial and nonspatial neural mechanisms underlying tactile spatial discrimination. In: von Euler C. Franzén O, Lindblom O, Ottoson D, ed. Somato-sensory Mechanisms. Plenum Press, New York, N.Y. 1984, pp. 237-248; and Connor C E, Hsiao S S, Phillips J R, Johnson K O. Tactile roughness: Neural codes that account for psychological magnitude estimates. J. Neuroscience 10 (1990) 3823-3836. Establishing the thresholds of these mechanoreceptor populations is thus required to define the tactile acuity of a skin site.

A technique has been developed for determining the sensitivity of SAI, FAI and FAII receptor populations at the fingertip using audiometric-like procedures, see our publication Brammer A J, Piercy J E. Measuring vibrotactile perception thresholds at the fingertips of power-tool operators. Proc UK Informal Group Meeting on Human Response to Vibration, Buxton, September 1991, pp. 1-8. An essential feature of the technique is to control contact between the skin and a vibrating probe. A procedure for measuring vibrotactile perception thresholds is then employed that permits the determination of the subject's performance.

Thresholds recorded in populations of power-tool operators exposed to hand-arm vibration have revealed two basic patterns of abnormality. This is discussed in the papers by Brammer A J, Piercy J E. Measuring vibrotactile perception thresholds at the fingertips of power-tool operators. Proc UK Informal Group Meeting on Human Response to Vibration,, Buxton, September 1991, pp. 107 and in Brammer A J, Piercy J E, Nohara S, Nakamura H, Auger P L, Haines A T, Lawrence M, Brubaker R L, van Netten C. Vibrotactile thresholds in operators of vibrating hand-held tools. In: Akada A, Taylor W, Dupuis H, ed. Hand-Arm Vibration. Kyoei Press, Kanazawa Japan 1990, pp. 221-223. One pattern involves threshold shifts of comparable magnitude at all frequencies, which is consistent with damage to the whole nerve. The second pattern involves threshold shifts at frequencies mediated by only one or two mechanoreceptor types, and is thus suggestive of selective damage to nerve fibers or nerve endings. The latter pattern, which occurs frequently among vibration-exposed workers, may hence be distinguished from whole nerve compression (e.g. carpal tunnel syndrome) by measuring mechanoreceptor-specific vibrotactile thresholds.

A problem with known methods and apparatus for measuring a subject response is the accuracy of the measurements and the interpretation thereof. They generally cannot detect and correct improper subject responses.

SUMMARY OF INVENTION

It is a feature of the present invention to provide a method of identifying vibrotactile perception thresholds of nerve endings at a skin site of a subject to assess sensory change in tactile sensory nerve function, and which is capable of identifying and quantifying errors and inconsistencies in the subject's response to obtain a substantially accurate representation of the results.

According to the above feature, from a broad aspect, the present invention provides a method of identifying vibrotactile perception thresholds of nerve endings of at least one mechanoreceptor nerve population at a skin site of a subject to assess sensory change in tactile sensory nerve function. The method comprises positioning a vibration generating means at a skin site to be tested. A plurality of sinusoidal bursts of a known frequency signal, separated by a quiescent period of time between bursts, is applied within a predetermined frequency range to the vibration generating means and at a known amplitude to apply a vibration force at the skin site. The amplitude is changed in an ascending and descending mode until a sensory response is received from the subject in both modes, and a first and second threshold signal value representative of a vibration amplitude respectively in ascending and descending modes is recorded, and a mean threshold signal value is obtained from the first and second threshold signal values. A deviation between the mean threshold signal value, and a stored reference mean threshold value representing tactile sensory nerve function of healthy subjects is then obtained to form a threshold shift value. A second known frequency signal, within the predetermined frequency range, is then applied at a known amplitude which is also changed until another sensory response is received from the subject to obtain a second set of threshold signal values. The deviation between the first and second threshold shift values corresponding respectively to the first and second sets of threshold values forms an inconsistency parameter value. This inconsistency parameter value is then compared with a stored reference inconsistency limit value to evaluate the acceptance or rejection of the first and second threshold signal values.

According to a still further broad aspect of the present invention, there is provided a system for identifying vibrotactile perception thresholds of nerve endings of at least one mechanoreceptive nerve population at a skin site of a subject to assess sensory change in tactile sensory nerve function. The system comprises vibration generating means having a contact element for positioning on the skin site and capable of being vibrated at specific frequencies. Frequency generating means is connected to the vibration generating means for supplying a known frequency signal within a predetermined frequency range to the vibration generating means. Control circuit means selects the known frequency signal and an amplitude thereof. The control circuit means modifies the amplitude of the known frequency signal in an ascending and descending mode. Switch means is actuable by the subject to provide response signals to the control circuit means and responsive to an ascending and a descending amplitude of the known frequency signal. The control circuit means has processing means for calculating a mean threshold signal value from the response signals and calculating a deviation between the mean threshold signal value and a stored reference mean threshold value. The stored reference mean threshold value represents tactile sensory nerve function of healthy subjects. The processing means by calculating the deviation obtains a threshold shift value. The control circuit means applies a second known frequency signal within the predetermined frequency range to obtain a second set of threshold values from the subject. The processing means calculates the deviation between first and second threshold shift values corresponding respectively to a first and second set of threshold values to obtain an inconsistency parameter value. This value is compared with a stored reference inconsistency limit value to evaluate the acceptance or rejection of the first and second threshold signal values.

More specifically, the present invention is concerned with the application of these signals to the fingertip of a subject to measure the vibrotactile perception of specialized nerve endings involved in the sense of touch. Two known frequency signals are applied within three frequency ranges, each frequency range corresponding to a different nerve ending population representative of the SAI, FAI and FAII type mechanoreceptors.

Further, in accordance with the invention, a plurality of sinusoidal bursts of the known frequency are generated at the known amplitudes and separated by quiescent periods of time, and responses are obtained in an ascending and descending amplitude mode.

BRIEF DESCRIPTION OF DRAWINGS

A preferred embodiment of the present invention will now be described with reference to the accompanying drawings in which.

DESCRIPTION OF PREFERRED EMBODIMENTS

Figure 1:
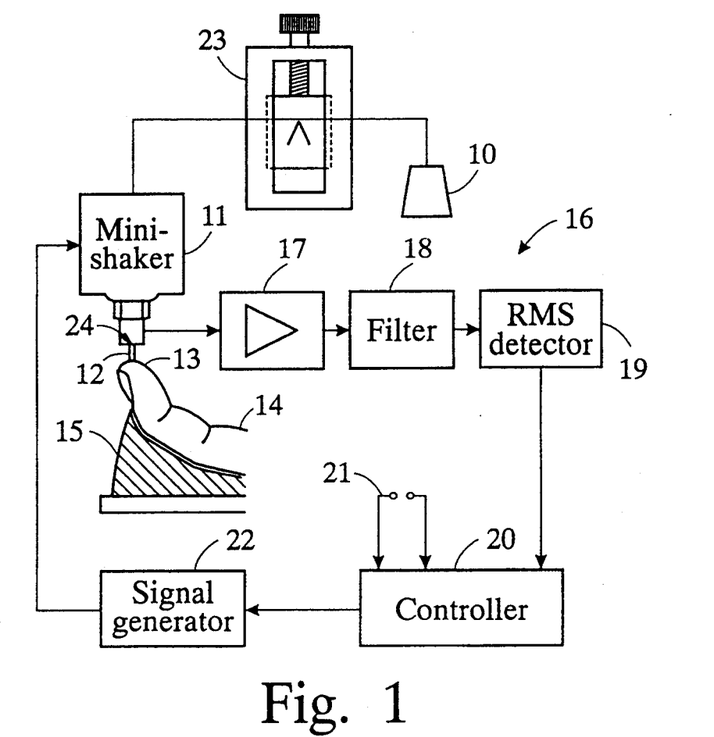
FIG. 1 is a block diagram illustrating a measurement system for carrying out the method of the present invention.

Referring now to the drawings, and more particularly to FIG. 1, there is shown generally at 10 an apparatus capable of carrying out the method of the present invention. The apparatus consists essentially of a vibration stimulator 11 which is a transducer capable of vibrating a probe 12 on the tip 13 (the skin site) of a subject's finger 14, preferably in an orientation normal to the tip 13. The end of the probe 12 is preferably flat and preferably has a circular section. The subject places his arm on an armrest 15 with the finger 14 pointing upwards, as illustrated.

An electronic circuit 16 comprising an amplifier 17, a noise filter 18 and an RMS detector 19 detects the root mean squared acceleration of the stimulus or probe 12 as measured by a motion sensor 24, which is an accelerometer in an example as shown in FIG. 1, and feeds signals representative thereof to a controller 20 for monitoring. The controller 20 may consist of a PC computer operated by a program to perform the various steps of the method of the present invention, as illustrated by FIGS. 6A to 6G. A switch 21, operated by the subject, feeds detection signals to the controller. The subject turns on the switch when a stimulating vibration is detected during an ascending amplitude mode of the frequency signal and also during a descending amplitude mode of that same signal, and turns off the switch when the stimulating vibration can no longer be felt. This may be repeated several times at the same frequency. The controller circuit 20 feeds a signal generator 22 which provides the amplitude and frequency of the signal driving the stimulator. A pressure adjusting mechanism 23 adjusts the position of the end of the probe 12 over the skin site, herein the fingertip 13, and also maintains a substantially constant static force thereon. An essentially constant static contact pressure between the probe tip and the skin surface, or indentation of the skin surface, is established by lowering the fulcrum of the pressure adjusting mechanism a measured distance.

During operation the controller performs the testing of the subject, and, accordingly, upon receipt of signals from the switch 21, will either change the amplitude or switch amplitude modes of the generated frequency signal, or change its frequency, or either repeat automatically the test, or advise the operator to repeat the test until a satisfactory mean threshold response is obtained.

It is pointed out that during measurements, the arm of the subject is supported horizontally with the finger being tested in a relaxed, curved position, with the palm upwards, as illustrated in FIG. 1. The probe 12 has a small diameter flat end which is lowered onto the fingertip from above by the pressure adjusting mechanism 23 until it contacts the skin with a substantially constant compressive force. Changes in thresholds with skin temperature are minimized by proper selection of the measurement frequencies and by temperature control of the measurement environment.

In the method of the present invention, sinusoidal bursts of vibration, of constant amplitude separated by quiescent periods, are applied to the skin site, herein the tip 13 of finger 14, at a selected frequency. Successive bursts initially increase in amplitude or intensity until the subject signals, by pressing the switch 21, that the stimulus has been detected. Successive bursts then decrease in intensity until the subject signals that the stimulus can no longer be felt, whereupon the burst intensity is, once again, increased. This cycling of burst intensity is repeated, and the mean threshold signal value for the onset and loss of tactile sensation is established by the known psychophysical method of limits.

Figure 2:
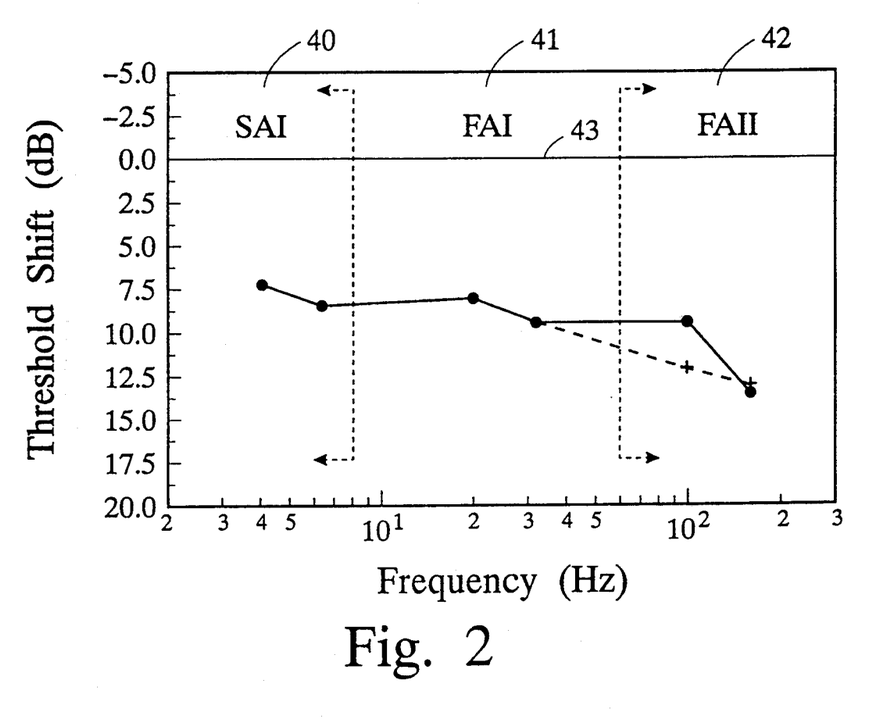
FIG. 2 is a tactogram showing threshold shift values measured from a finger of a subject.

Measurements are performed at six specific frequencies, chosen so that each mechanoreceptor population mediates the threshold at two frequencies. By introducing reference mean threshold values from a medically screened population, free from signs, symptoms or history of peripheral neuropathy, the thresholds determined at an individual's fingertip may be expressed as a "tactogram", as shown in FIG. 2, in which a reference mean threshold value is indicated by line 43. This graphical representation of the data displays the change in mechanoreceptor-specific threshold from the reference mean threshold value for normal hands at that frequency. A tactogram thus expresses the acuity, relative to normal hands, of three populations of specialized nerve endings involved in the sense of touch, namely, the SAI, FAI and FAII populations, as shown at 40, 41 and 42.

The following are examples of tests performed on different subjects.

EXAMPLE I

Figure 3:
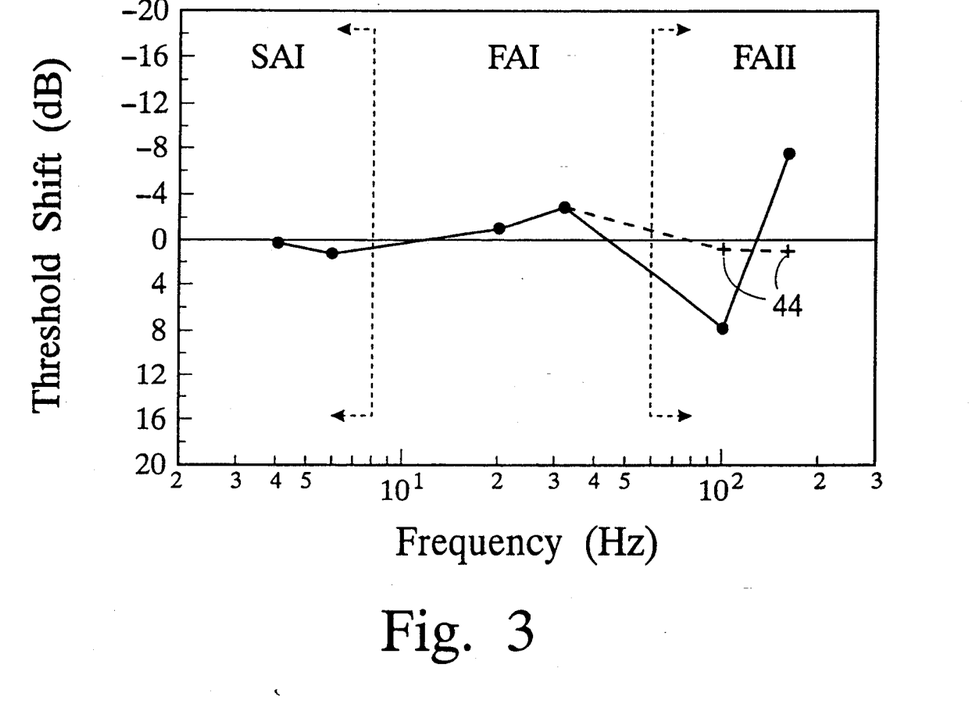
FIGS. 3 to 5 are further tactograms plotted from various subjects tested.

In reference to FIG. 3, there is illustrated results of a test in which an inconsistency was detected by the controller in the thresholds mediated by the receptors. It can be seen that the threshold shifts recorded at frequencies mediated by the SAI receptors are similar (viz. 0.3 dB at 4 Hz, and 1.2 dB at 6 Hz). An identical threshold shift at all frequencies mediated by the same mechanoreceptor population is expected. The threshold shifts recorded from the FAI receptors differ by 1.9 dB (viz. −1.0 dB at 20 Hz, and −2.9 dB at 32 Hz), a margin currently considered acceptable compared to a reference inconsistency limit value for the FAI receptors.

An example of inconsistency limit values for SAI, FAI and FAII is shown in Table 1. To get these inconsistency limit values, thresholds were obtained from the fingertips of healthy males, aged from 24 to 67 years, without signs, symptoms or history of neurological disease, or of exposure to vibration. The results presented in Table I are for fingers innervated by the median nerve (usually digit 3, left and right hands), as data from the median, and ulnar, nerves could not be distinguished in these subjects. The measurements commenced with a short training session in which each subject was presented sequentially with tests at the same frequencies for each receptor population, the frequencies of 4 Hz and 6 Hz for the SAI, 20 Hz and 32 Hz for the FAI, and 100 Hz and 160 Hz for the FAII receptors.

TABLE 1

Intra-Subject Threshold Variability
Recorded in Five Healthy Male Subjects (in dB)

| Subject | Age (yr) | SAI | FAI | FAII |
|---------|----------|-----|-----|------|
| 1 | 24 | 2.7 | 3.0 | 3.1 |
| 2 | 38 | 1.7 | 1.3 | 1.6 |
| 3 | 41 | 1.2 | 1.8 | 1.5 |
| 4 | 49 | 2.0 | 2.4 | 2.7 |
| 5 | 67 | 2.0 | 1.9 | (5.2) |
| Mean | | 1.9 | 2.1 | 2.2 |

In Table 1 the mean intra-subject variability is expressed as the standard deviation of the thresholds obtained at each frequency and, displays a modest dependence on receptor type. Differences in variability were, however, observed between subjects. In these measurements, the largest variability occurred at frequencies mediated by the FAII receptors of subject #5. With this exception, the within subject variability was relatively insensitive to frequency (and hence also receptor type) and was 2.1±0.6 dB.

Returning to FIG. 3, the inconsistency of 15.2 dB in the threshold shifts recorded from the FAII receptors (viz. +7.7 dB at 100 Hz compared with −7.5 dB at 160 Hz) is not acceptable but resolved by repeating the measurements. The repeated measurement, the results of which are illustrated by the crosses 44 reveal that both initial thresholds were in error.

The process may be continued until acceptable agreement is obtained at frequencies mediated by each receptor population. For this reason, a subject is not informed of his/her performance until after all measurements have been completed. It is pointed out that instead of obtaining the required inconsistency limit value from intra-subject threshold variability data, it is possible to use inter-subject threshold variability data previously obtained in a manner, as described in the following Example 2.

EXAMPLE II

Figure 4:
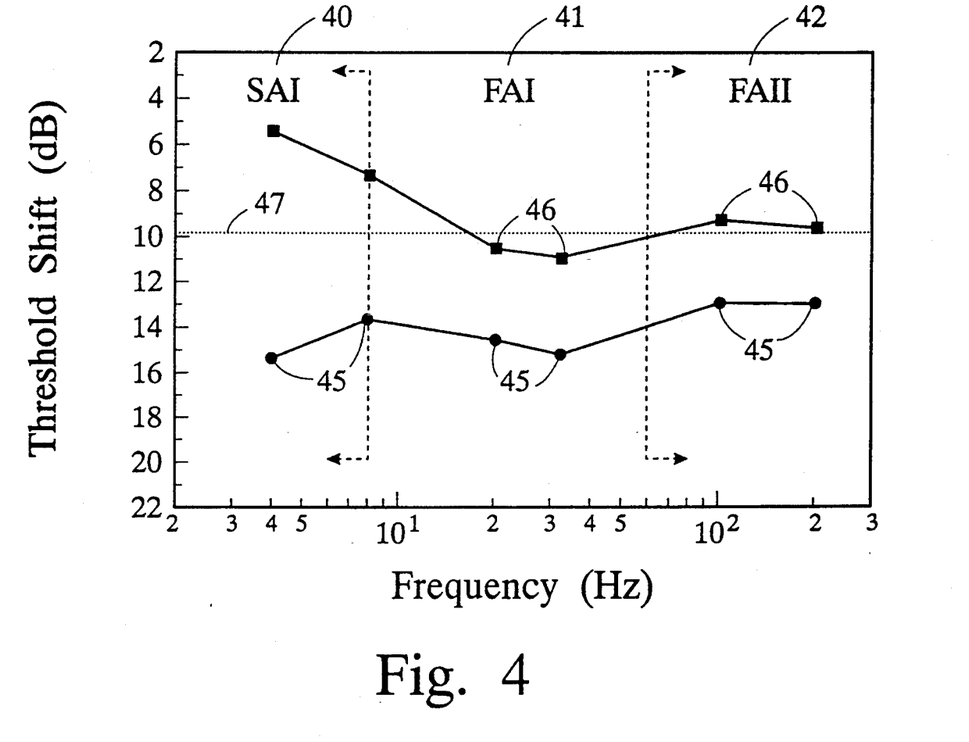

FIG. 4 illustrates results from tests of power-tool operators exposed to hand-arm vibration, and these show a first basic pattern of abnormality. This first pattern involves threshold shifts of comparable magnitude at all frequencies, which would appear to be consistent with damage to the whole nerve. An example of this pattern of sensory loss is shown by the results of the plotted circles 45, representative of digit 3. Results of the plotted squares 46, representative of digit 5, are borderline normal. In this diagram the data have been plotted as a tactogram, with normative deviation values, shown by dotted lines 47, as could be derived from intra-subject or inter-subject threshold variability, and accordingly corresponding to two standard deviations from the mean value recorded in normal hands of healthy subjects.

TABLE 2

Inter-Subject Threshold Variability in Three Population Groups Consisting of Healthy Males

| POPULATION GROUP | | STANDARD DEVIATION Receptor Type | | |
|---|---|---|---|---|
| Group # | Number of Hands | SAI | FAI | FAII |
| 1 | 23–25 | 5.2 | 4.9 | 3.7 |
| 2 | 29 | 4.6 | 4.8 | 4.8 |
| 3 | 34 | 4.5 | 5.0 | 6.1 |
| Mean | | 4.8 | 4.9 | 4.9 |

Table 2 shows an example of inter-subject threshold variability data which could be used to derive normative deviation values 47. To get this data, thresholds were measured at the fingertips of three groups of male workers (right and left hands). Two groups were formed from Japanese white-collar workers, and consisted of: 1) university and professional workers, with mean age 34±5.9 years (N=23–25); and 2) a group drawn from the general population, with mean age 62±5.6 years (N=29). The third group was formed from North American laboratory, and manual, workers, with mean age 41±11 years (N=34).

Figure 5:
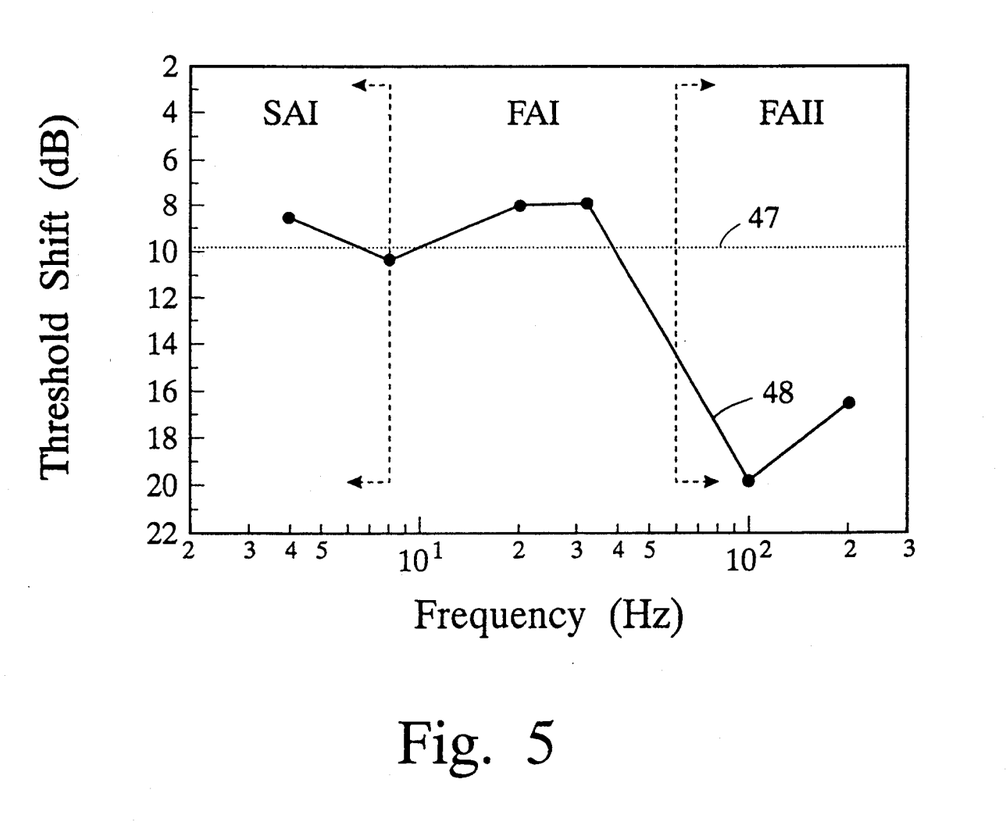

When the results were grouped by age, the inter-subject variability, expressed as the standard deviation of the thresholds obtained at each frequency, differed somewhat between age groups and measurement frequencies. The mean variability in threshold recorded from the three population groups is shown by receptor type in Table 2, and was 4.8±0.6 dB. Accordingly, a unique normative deviation value of 9.6 dB is illustrated in FIGS. 4 and 5 at numeral 47, in which case a normalization step, as proposed in a second embodiment of the method of the present invention, is not required. However, groups of workers having different age or occupation characteristics can provide inter-subject variability results which show variations between age/occupation groups and measurement frequency (see, for example, group 1 in Table 2).

In order to take into account variations of normative standard deviation values as a function of frequency, it is proposed to normalize the deviation between the mean threshold signal value and a stored reference mean threshold value representing tactile sensory nerve function of healthy subjects, by calculating the ratio of this deviation to the reference normative deviation value for the measurement frequency, to obtain the desired threshold shift value representing an inconsistency test value. This step will be later explained in more detail with reference to FIGS. 6D to 6G. It is pointed out that instead of obtaining the required inter-subject threshold variability data, it is possible to use intra-subject threshold variability data previously obtained in a similar manner, as described with reference to the preceding Example 1.

EXAMPLE III

The second pattern of abnormalities involves threshold shifts at frequencies mediated by only one or two mechanoreceptor types. FIG. 5 shows abnormal threshold shifts 48 at frequencies mediated by only one receptor type and is thus suggestive of selective damage to nerve fibers or nerve endings.

The subjects providing the data in FIGS. 4 and 5 were employed as forest workers and regularly operated chain saws. Neither subject had operated a chain saw for at least a week prior to the vibrotactile measurements.

The pattern of loss exemplified by FIG. 5 has been more commonly observed among chain-saw operators. It would thus appear that operation of at least some vibrating power tools may result in changes to nerves which affect receptor populations selectively. Such changes may readily be identified by means of a mechanoreceptor-specific measurement, and tactogram. Whole nerve sensory dysfunction, such as occurs in some diseases, and commonly from localized nerve compression at the wrist (e.g. carpal tunnel syndrome), may possibly also be inferred from a tactogram (e.g. digit 3 in FIG. 4 which possesses an abnormal threshold while digit 5 is borderline normal). Hence the pattern of loss revealed by a tactogram may provide information on the nature of a nerve injury.

The following Tables 3, 4 and 5 give examples of the threshold signal values which are recorded upon repeating tests at a specific frequency in the ascending and descending amplitude modes in order to obtain (a) upper and/or lower threshold deviations, and (b) intra-receptor threshold deviations, and then arrive at a mean threshold signal value to substantially eliminate inconsistencies in the response.

The "upper" and "lower" thresholds in the Table are mathematically represented by ut(k) and lt(k), respectively, where k=1,2,..., 6. The average thresholds are first computed separately for the ascending and descending modes and exclude the first upper and lower values, ut(1) and lt(1), respectively. These average thresholds are listed in the Table as the "aver. exclud. #1".

TABLE 3

Stimulus on 0.8 (s)

| FREQ (Hz) 32 | THRESHOLDS (dB re 0.1 m/s/s RMS) | |
|---|---|---|
| | UPPER | LOWER |
| | +0.7 | −20.1 |
| | +6.4 | −15.7 |
| | −0.8 | −15.9 |
| | +2.8 | −15.9 |
| | +6.4 | −15.9 |
| | +0.0 | +0.0 |
| AVER EXCLUD. #1 | +3.7 | −15.8 |
| MEAN THRESHOLD: −6.1 | | |

TABLE 4

Stimulus on 1.6 (s)

| FREQ (Hz) 6 | THRESHOLDS (dB re 0.1 m/s/s RMS) | |
|---|---|---|
| | UPPER | LOWER |
| | −20.0 | −32.8 |
| | −22.5 | −31.4 |
| | −22.0 | −30.3 |
| | −20.4 | −27.6 |
| | +0.0 | +0.0 |
| | +0.0 | +0.0 |
| AVER.EXCLUD. #1 | −21.6 | −29.9 |
| MEAN THRESHOLD: −25.7 | | |

TABLE 5

Stimulus on 0.8 (s)

| FREQ (Hz) 100 | THRESHOLDS (dB re 0.1 m/s/s RMS) | |
|---|---|---|
| | UPPER | LOWER |
| | +12.5 | −0.6 |
| | +12.1 | −0.6 |
| | +12.1 | +1.9 |
| | +14.6 | +4.5 |
| | +0.0 | +0.0 |
| | +0.0 | +0.0 |
| AVER.EXCLUD. #1 | +13.0 | +2.0 |
| MEAN THRESHOLD: +7.5 | | |

The following Table 6 is an example of a data summary that may be displayed on the screen of a PC computer, which may serve as the controller 20, or printed on an associated printer (not shown), or transmitted for use by someone else.

TABLE 6

| RECORD | FREQ. | THRESHOLD | THRESHIFT | SHIFT/NORM. VALUE | ERROR TYPE |
|---|---|---|---|---|---|
| 33 | 160 | +12.6 | +0.2 | +0.04 | |
| 34 | 32 | +4.0 | +5.6 | +1.12 | 1,2,3 |
| 35 | 6 | −20.7 | +0.7 | +0.14 | |
| 36 | 100 | +10.8 | −1.5 | −0.31 | |
| 37 | 20 | −7.1 | +1.8 | +0.36 | 2,3 |
| 38 | 4 | −22.6 | +0.3 | +0.06 | |
| 39 | 32 | +1.8 | +3.4 | +0.67 | 1 |

The summary data provides record identification, the frequency at which the test was performed, the average or mean threshold, the calculated threshold shift relative to a reference mean threshold value for healthy subjects, the shift compared to normative deviation values, and the error type.

The column entitled "threshold" contains the "mean threshold" values computed from tables such as those shown as examples of threshold signal values (Tables 3-5). The column entitled "shift/norm value" contains computed values of the ratio of the threshold shift values to a stored reference normative deviation value for the measurement frequency. The stored reference normative deviation values may be derived from a knowledge of the art, or from the intra-subject or inter-subject threshold variability of healthy subjects. As earlier mentioned, in circumstances in which the stored reference deviation values at different frequencies are identical, the normalizing factor will be the same at each frequency. To the extent that this common factor appears equally on both sides of equations used in computations it may be canceled.

The sequence of seven measurements shown in records 33 to 39 illustrates another application of inconsistency detection. Record 34 shows a measurement at a frequency of 32 Hz in which the computer has analyzed the differences between individual upper thresholds, individual lower thresholds, and pairs of upper and lower thresholds, and ascribed errors type 1 and 2 to the data when stored reference difference limit values u and w, respectively, have been exceeded. The stored reference difference limit values may be derived from a knowledge of the art, or from the statistical variability of the ut(k) and/or lt(k) or the intra-subject threshold variability of healthy subjects. Record 37 shows a measurement at a second frequency, namely 20 Hz, mediated by the same receptor as record 34 during which an error type 2 occurred. Reference to records 34 and 37 shows that the shift/norm value was +1.12 and 0.36, respectively. The difference between these values defines the magnitude of the inconsistency parameter, which in this case exceeds a stored reference inconsistency limit value, thereby resulting in an error type 3 being ascribed to the data in records 34 and 37. To reduce the discrepancy between the results of these measurements, it is necessary to repeat the measurements at one or both frequencies employed in records 34 and 37, namely 20 or 32 Hz in this example. In order to minimize the number of measurements performed at each skin site, it is desirable for the operator or computer to identify which record is most likely to be in error. This decision may be made by the operator from a knowledge of the art, or from the presence of type 1 or 2 errors associated with a record, and by the computer from the presence of type 1 or 2 errors. Based on the information in records 34 and 37, which show more errors occurred in record 34 than 37, the measurement was repeated at the frequency of record 34, namely 32 Hz. The results of the repeated measurement, shown in record 39, reveal that the new inconsistency parameter computed between records 37 and 39 is now less than the inconsistency limit value, so that the error type 3 has been eliminated and the consistency of the measurements on this receptor thereby substantially improved. In addition, the results of record 34 may now be deduced as being in error.

Figure 6A:
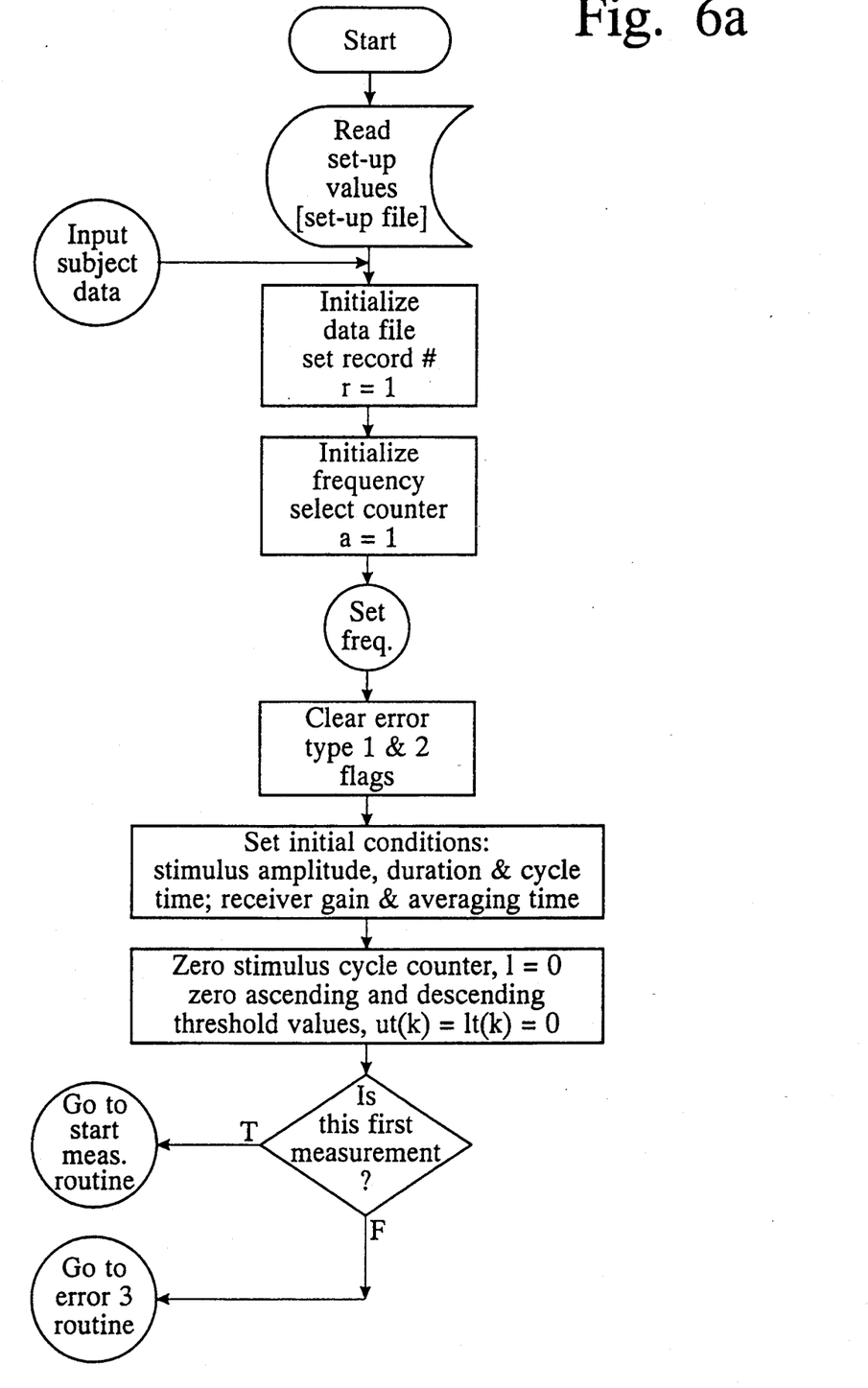
FIGS. 6A to 6G are flow charts illustrating the operation of a computerized system according to the method of the present invention.
Figure 6B:
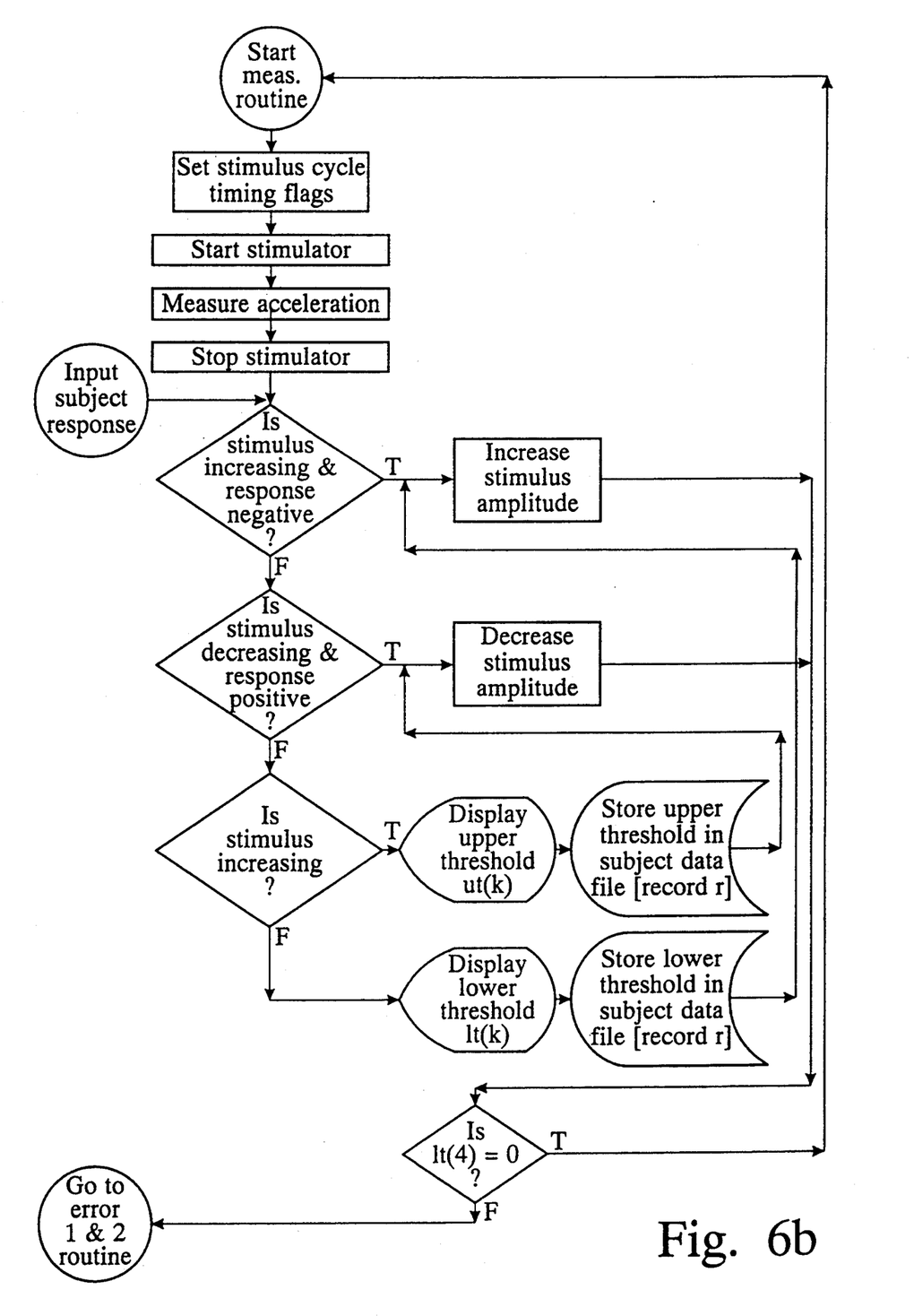
Figure 6C:
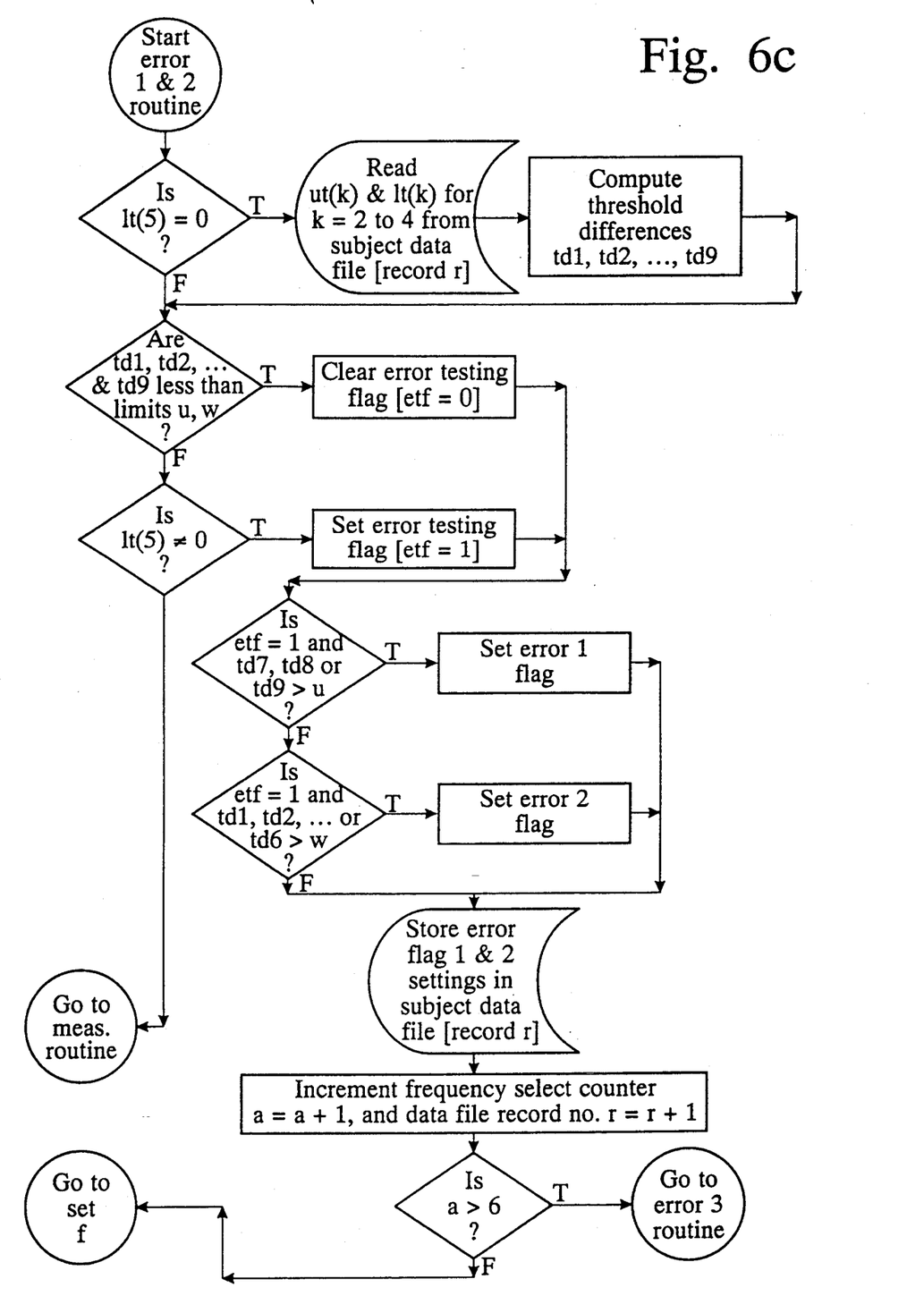
Figure 6D:
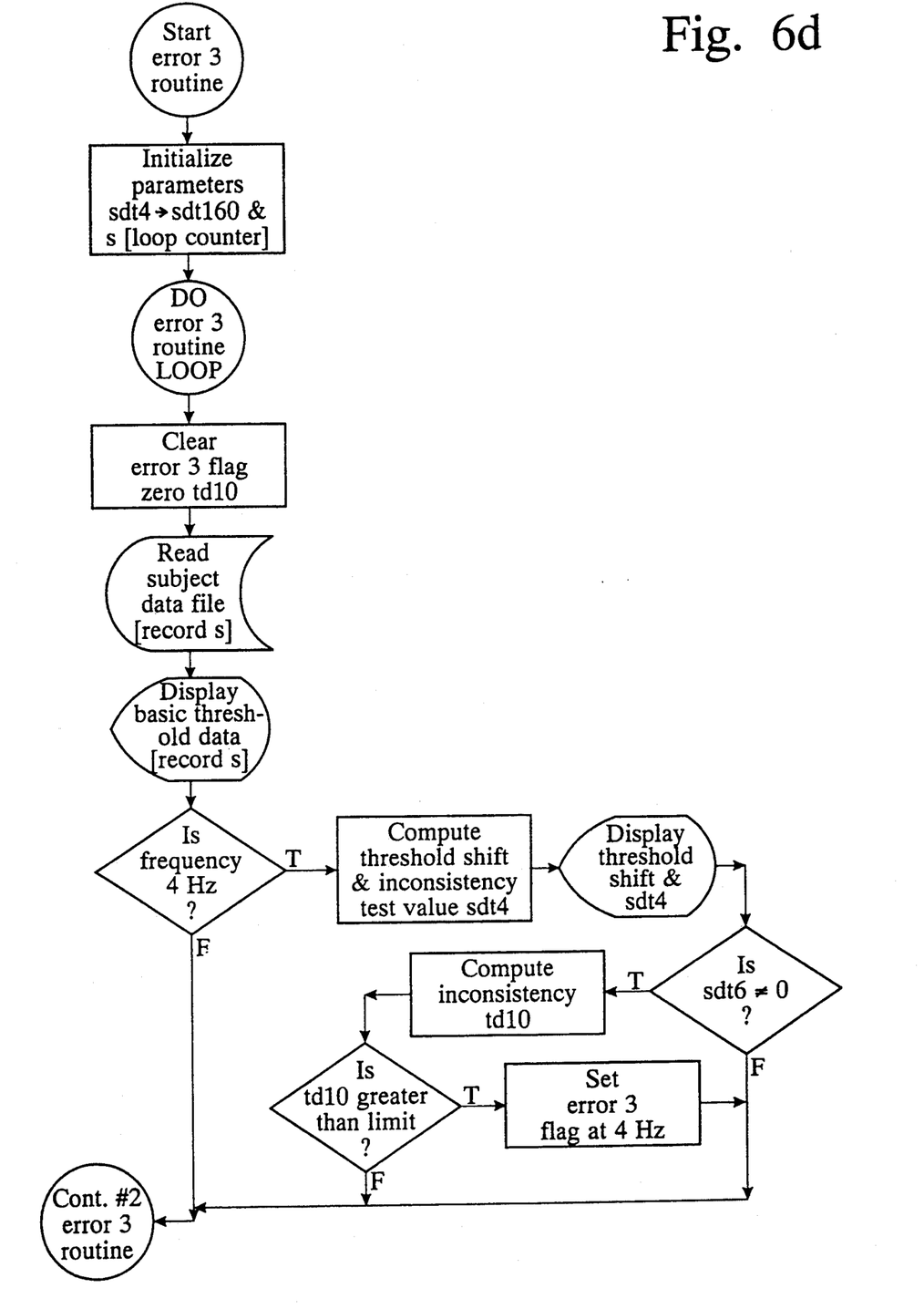
Figure 6E:
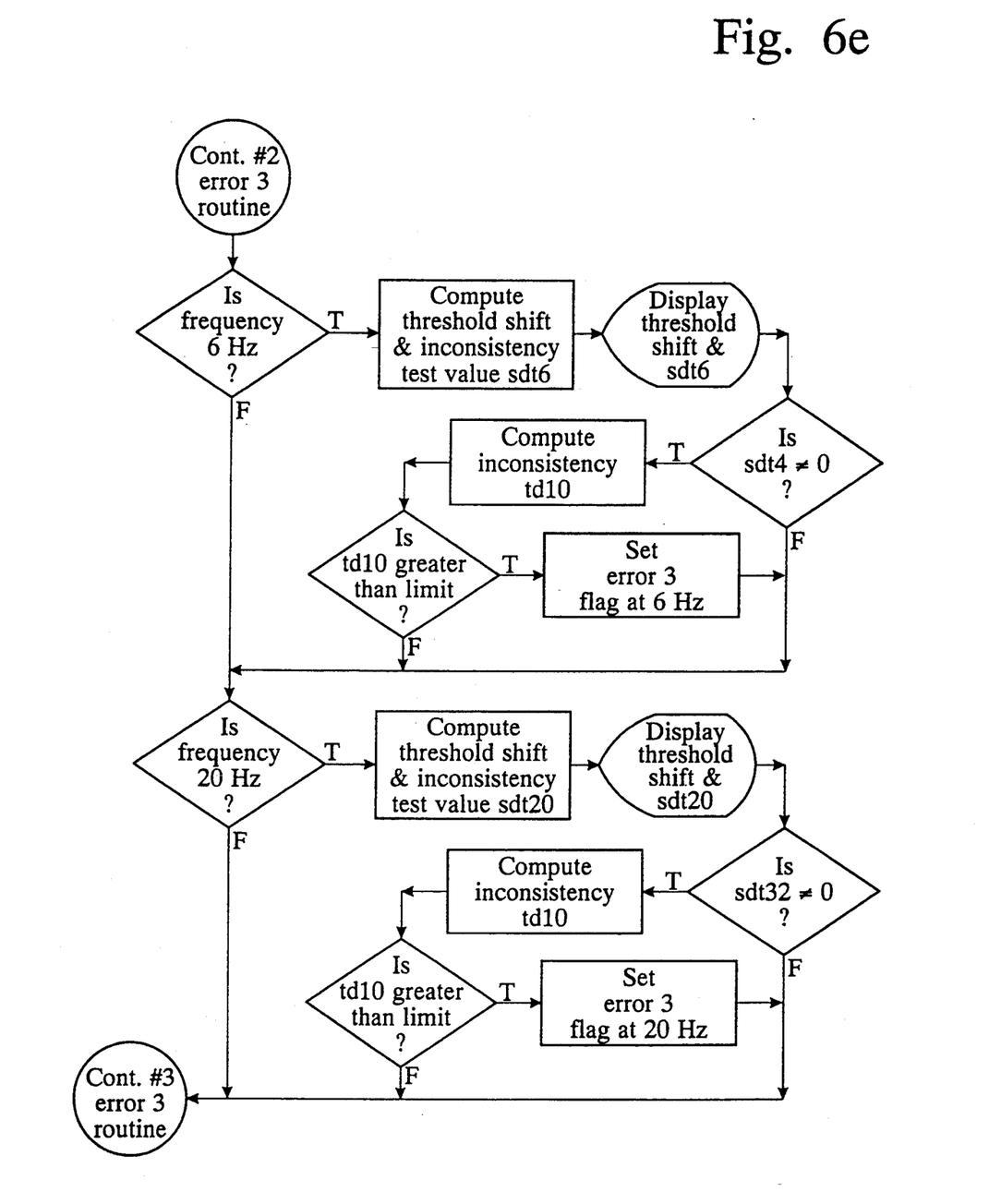
Figure 6F:
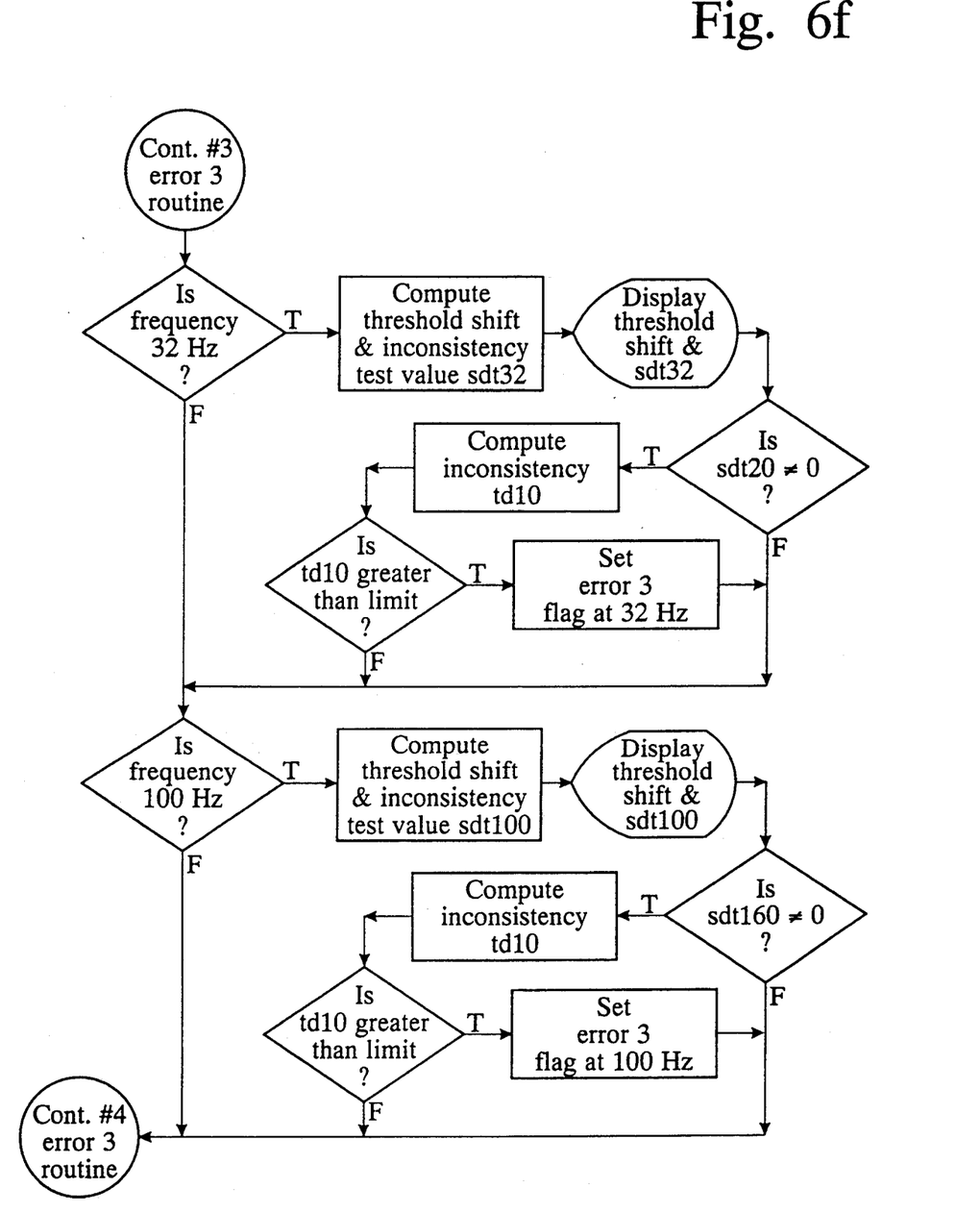
Figure 6G:
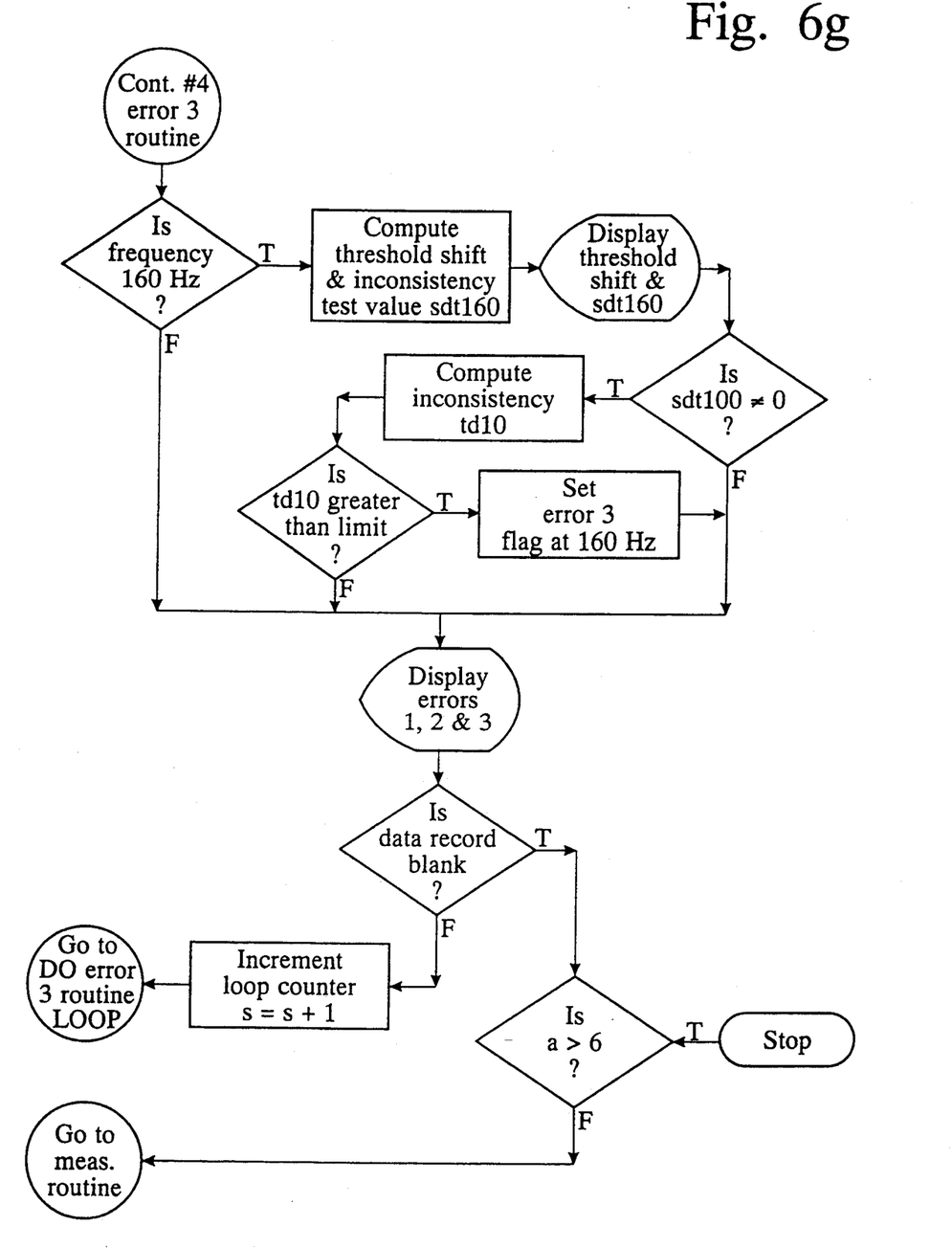

FIGS. 6A to 6G are flow charts illustrating the operation of a computer controlled system capable of carrying out the method of the present invention after the body part containing the skin site to be tested has been supported, and appropriate conditions for stimulating the skin surface established. Briefly described, FIG. 6A illustrates various steps performed by the computer for start-up and initializing procedures. As can be seen, the computer first reads a set-up file, which defines available measurement parameters such as stimulus burst durations and quiescent intervals, test frequencies, reference mean thresholds and reference normative deviation values for healthy hands, threshold difference limit values, and the inconsistency limit values. Personal information concerning the subject is entered and a subject data file established. The computer then resets the measurement system and sets initial conditions in preparation for the measurement including signal cycle, frequency and amplitude. FIG. 6B illustrates the addressing sequence for measuring responses in both ascending and descending modes, for the input of the response from the subject, and for detecting, displaying, and recording to file the upper and lower thresholds ut(k) and lt(k), respectively. FIG. 6C illustrates the addressing sequence for computing errors types 1 and 2 from comparisons of threshold differences td1, td2, . . . , td9 constructed from the upper and lower thresholds. A possible implementation of this procedure is to compute the threshold differences from:

$$td1 = |ut(2) - ut(3)|$$
$$\text{-etc.-}$$
$$td6 = |lt(4) - lt(2)|$$
$$td7 = |[ut(2)] + lt(2)] - [ut(3) + lt(3)]|/2 \text{ -etc.-}$$

An error type 1 occurs when td7, td8 and/or td9 exceed(s) the stored reference limit value u, and an error type 2 occurs when td1, td2, . . . and/or td6 exceed(s) the stored reference limit value w. FIGS. 6D, 6E, 6F and 6G illustrate the addressing sequence for computing inconsistencies in vibrotactile thresholds by means of error type 3 from measurements conducted at different frequencies mediated by the same mechanoreceptor population. A threshold shift value is computed from the mean threshold signal value measured at one frequency and a stored reference mean value obtained from healthy persons at that frequency. In a preferred embodiment of the present invention the threshold shift value is then normalized by a stored reference normative deviation value applicable to that frequency, to form a normalized threshold shift value representing an inconsistency test value at that frequency. An inconsistency parameter is then computed from the inconsistency test values at different frequencies. A possible implementation of this procedure is to compute inconsistency test values at each measurement frequency, sdt4, sdt6, . . . , sdt160, where, for example, sdt4 and sdt6 are obtained at frequencies mediated by the same receptor population. The inconsistency parameters may then be computed from the inconsistency test values at two frequencies mediated by the same receptor population, such as, for example:

$$td10 = |sdt4 - sdt6|.$$

An error type 3 occurs when td10 exceeds the stored inconsistency limit value. All numerical computations in these illustrations are envisaged to involve floating-point arithmetic. Other features of the charts shown in FIGS. 6A to 6G are self-explanatory to persons skilled in the art and need not be discussed in more detail herein.

There are numerous potential applications for the method of the present invention using the apparatus described or other suitable apparatus capable of carrying out the method. Some of these include, for example:

A. Industrial Hygiene/Occupational Medicine

Tingling, numbness and other disturbances in hand function frequently occur in occupations involving manual or clerical work. Many of these disturbances involve temporary or persistent tactile loss (e.g. vibration-induced neuropathy, carpal tunnel syndrome, and repetitive strain injuries). Exposure to neurotoxic chemical substances may also lead to peripheral sensory loss in the legs and arms. Potential applications for the method hence include:

1. pre-employment and ongoing (e.g. annual) medical monitoring of persons in occupations in which peripheral tactile loss may occur;
2. assessing tactile acuity for compensation purposes;
3. providing tactile information for epidemiologic studies of working populations; and
4. providing information on patterns of tactile sensory loss, and hence insight into the possible origins of nerve injuries.

B. Clinical Medicine

Quantitative sensory testing, which includes the determination of vibrotactile perception thresholds, is an important method for establishing peripheral sensory function. Most of the existing devices for determining vibrotactile thresholds are used for such purposes. Applications for the method therefore include:

1. following the course of peripheral sensory nerve function in systemic neurological diseases (e.g. diabetes); and
2. establishing peripheral sensory nerve function in neurological and rehabilitation clinics.

By establishing the acuity of different mechanoreceptor populations, the method is especially suited to the following applications:

1. detecting patterns of tactile sensory loss, for use in differential diagnosis (e.g. receptor-specific loss);
2. monitoring peripheral sensory nerve function after nerve injury or surgical repair (e.g. selective reinnervation of nerve endings); and
3. establishing mechanoreceptor acuity and hence the potential for undertaking specific tactile tasks, including tactile communication.

The method may also be extended to (a) explore the role of mechanoreceptor acuity in the mechanisms and mechanics of touch; (b) establish relationships between receptor-specific vibrotactile thresholds and other measures of tactile performance, and manual dexterity; (c) establish performance measures in comparison with other methods for evaluating peripheral tactile function (such as sensitivity and specificity); (d) establish diseases and conditions in which selective sensory loss occurs, for use in differential diagnosis, in both clinical and occupational medicine; (e) establish sensory thresholds at different body sites for normal persons, as a function of age, sex, and other variables; and (f) explore the influence of mechanoreceptor acuity on schemes for tactile communication and virtual haptic environments.

It is within the ambit of the present invention to cover any obvious modifications, provided such modifications fall within the scope of the appended claims.

We claim:

1. A method of identifying vibrotactile perception thresholds of nerve endings of at least one mechanoreceptive nerve population at a skin site of a subject to assess sensory change in tactile sensory nerve function, said method comprising the steps of:

(i) supporting the body part containing the skin site of the said subject to be tested;

(ii) positioning a vibration generating means at a skin site to be tested of said subject in a manner to control contact between said vibration generating means and said skin surface;

(iii) applying a plurality of sinusoidal bursts of a known vibration frequency signal and separated by a quiescent period of time between bursts within a predetermined frequency range by said vibration generating means and at a known vibration amplitude to apply a vibration force to said skin site;

(iv) changing said vibration amplitude in ascending and descending modes until a sensory response is received from said subject in both modes and recording first and second threshold signal values representative of a vibration amplitude respectively in said ascending and descending modes;

(v) obtaining a mean threshold signal value from said first and second threshold signal values;

(vi) calculating deviation between said mean threshold signal value and a stored reference mean threshold value representing said tactile sensory nerve function of healthy subjects to obtain a threshold shift value;

(vii) applying a second known frequency signal within said predetermined frequency range and repeating steps (iv) to (vi) to obtain a second set of threshold values from said subject;

(viii) calculating deviation between first and second threshold shift values corresponding respectively to a first and second set of threshold signal values to obtain an inconsistency parameter value;

(ix) comparing said inconsistency parameter value with a stored reference inconsistency limit value to evaluate the acceptance or rejection of said first and second set of threshold signal values; and (x) presenting the results of measured sets of said threshold signal values.

2. A method as claimed in claim 1 further comprising the step of repeating said steps (iii) to (x) and (a) calculating deviation between said first and second threshold signal values to obtain a difference parameter value, and (b) comparing said difference parameter value with a stored reference difference limit value to evaluate further the acceptance or rejection of said first and second set of threshold signal values, if said inconsistency parameter value is unacceptable.

3. A method as claimed in claim 1 or 2 further comprising the steps of repeating said step (vii) and (viii) to (x) if said inconsistency parameter value is unacceptable.

4. A method according to claim 2 wherein said reference difference limit value is obtained from the statistical variability of said first and second threshold signal values or said intra-subject variability of healthy subjects.

5. A method as claimed in claim 1 or 2 wherein said step (vi) comprises the steps of (a) calculating the deviation between said mean threshold signal value and a stored reference mean threshold value representing tactile sensory nerve function of healthy subjects, and (b) normalizing said deviation by calculating the ratio of said deviation to a reference normative deviation value for said frequency to obtain said threshold shift values.

6. A method as claimed in claim 1 wherein said step (ii) comprises positioning said vibration generating means at a fingertip of said subject to measure the vibrotactile perception of specialized nerve endings involved in the sense of touch.

7. A method as claimed in claim 1 wherein said step (ii) further comprises applying a substantially constant static force on said skin site.

8. A method as claimed in claim 1 wherein said step (ii) further comprises providing a substantially constant skin indentation to said skin site.

9. A method as claimed in claim 6 wherein said steps (iii) to (x) are repeated at two known frequency signals within three frequency ranges, said frequency ranges corresponding to vibrotactile perception of different nerve ending populations in the groups identified as SAI (slow adapting type I), FAI (fast adapting type I), and FAII (fast adapting type II).

10. A method according to claim 1 wherein said reference inconsistency limit value is obtained from intra-subject or inter-subject threshold variability of healthy subjects.

11. A method according to claim 5 wherein said reference normative deviation value is obtained from inter-subject or intra-subject threshold variability of healthy subjects.

12. A method according to claim 1 wherein said step (iv) comprises the steps of (a) increasing said amplitude with each group of said bursts of vibration at said known frequency until said sensory response of the presence of said vibration is detected by said subject to obtain an ascending threshold signal, (b) decreasing said amplitude of said bursts at said known frequency until a further sensory response of the absence of said vibration is detected by said subject to obtain a descending threshold signal, and (c) calculating said mean threshold signal value from said ascending threshold value and said descending threshold value, and (d) repeating step (iv) several times to establish an average mean threshold signal value to constitute said mean threshold signal value.

13. A method as claimed in claim 9 wherein said step (ii) comprises positioning said vibration generating means at different fingertips of said subject and repeating steps (iii) to (x) to detect abnormalities of said nerve ending populations.

14. A method as claimed in claim 9, wherein there is further provided the step of (xi) producing a table or a chart of said recorded mean threshold signal values.

15. A method as claimed in claim 14 wherein said table further provides said known frequencies and said corresponding threshold shift values.

16. A method as claimed in claim 15 wherein said table further provides an indication of the acceptance or rejection of said first and second threshold signal values.

17. A method as claimed in claim 14 wherein said chart is a tactogram chart, said tactogram chart showing said threshold shift values compared to said reference normative deviation values corresponding to said frequencies.

18. A method as claimed in claim 8 wherein said two known frequencies of said SAI range are about 4 Hz and 6 Hz, of said FAI range about 20 Hz and 32 Hz, and of said FAII range about 100 Hz and 160 Hz.

19. A system for identifying vibrotactile perception thresholds of nerve endings of at least one mechanoreceptive nerve population at a skin site of a subject to assess sensory change in tactile sensory nerve function, said system comprising support means for supporting a body part containing said skin site of the said subject to be tested, vibration generating means having a contact element for positioning on said skin site in a manner to control contact between said vibration generating means and said skin site, said vibration generating means being vibrated at specific frequencies, frequency generating means connected to said vibration generating means for supplying a known frequency signal within a predetermined frequency range to said vibration generating means, control circuit means to select said known frequency signal and an amplitude thereof, said control circuit means modifying amplitude of said known frequency signal in an ascending and descending mode switch means actuable by said subject to provide response signals to said control circuit means and responsive to an ascending and a descending amplitude of said known frequency signal, said control circuit means having processing means for obtaining a mean threshold signal value from said response signals and a deviation between said mean threshold signal value and a stored reference mean threshold value representing tactile sensory nerve function of healthy subjects to obtain a threshold shift value, said control circuit means applying a second known frequency signal within said predetermined frequency range to obtain a second set of threshold values from said subject, said processing means obtaining the deviation between first and second threshold shift values corresponding respectively to a first and second set of threshold values to obtain an inconsistency parameter value, comparing said value with a stored reference inconsistency limit value to evaluate the acceptance or rejection of said first and second threshold signal values.

* * * * *